United States Patent
Quan et al.

(10) Patent No.: US 10,232,158 B2
(45) Date of Patent: Mar. 19, 2019

(54) MICRONEEDLE PATCH APPLICATION DEVICE AND PATCH HOLDER

(71) Applicant: COSMED PHARMACEUTICAL CO., LTD., Kyoto, Kyoto (JP)

(72) Inventors: Ying-shu Quan, Kyoto (JP); Fumio Kamiyama, Kyoto (JP)

(73) Assignee: COSMED PHARMACEUTICAL CO., LTD., Kyoto (JP)

( * ) Notice: Subject to any disclaimer, the term of this patent is extended or adjusted under 35 U.S.C. 154(b) by 0 days.

(21) Appl. No.: 15/022,169

(22) PCT Filed: Sep. 18, 2013

(86) PCT No.: PCT/JP2013/075149
§ 371 (c)(1),
(2) Date: Mar. 15, 2016

(87) PCT Pub. No.: WO2015/040697
PCT Pub. Date: Mar. 26, 2015

(65) Prior Publication Data
US 2016/0235958 A1    Aug. 18, 2016

(51) Int. Cl.
*A61M 37/00*    (2006.01)
(52) U.S. Cl.
CPC . *A61M 37/0015* (2013.01); *A61M 2037/0023* (2013.01); *A61M 2205/8281* (2013.01)
(58) Field of Classification Search
CPC ...... A61M 2037/0023; A61M 37/0015; A61M 2025/8281
See application file for complete search history.

(56) References Cited

U.S. PATENT DOCUMENTS

| 2004/0064087 A1* | 4/2004 | Lastovich | A61B 17/205 604/46 |
| 2005/0096586 A1* | 5/2005 | Trautman | A61B 17/205 604/46 |

(Continued)

FOREIGN PATENT DOCUMENTS

| CN | 1691969 A | 11/2005 |
| CN | 101060882 A | 10/2007 |

(Continued)

OTHER PUBLICATIONS

Supplementary European Search Report for the Application No. EP 13 89 4024 dated May 3, 2017.

(Continued)

*Primary Examiner* — Jenna Zhang
(74) *Attorney, Agent, or Firm* — Cheng Law Group, PLLC

(57) ABSTRACT

Provided is a device for surely and easily applying a microneedle patch to a skin.
In a case body 2, a pressing member 3 having a tip surface 3a is disposed such that the pressing member is biased in a first direction X1 by a first biasing member. The movement in the first direction X1 is locked by a locking member 7 and a locking part 3g so that the pressing member 3 is brought into a locked state. The locked state is released by pressing a tip of a lock-releasing member 11 against the skin. When the locked state is released, a tip surface 3a of the pressing member 3 is moved in the first direction X1 and the tip surface 3a applies the microneedle patch to the skin.

10 Claims, 9 Drawing Sheets

(56) References Cited

U.S. PATENT DOCUMENTS

| | | | |
|---|---|---|---|
| 2005/0261631 A1* | 11/2005 | Clarke | A61K 9/0021 604/173 |
| 2008/0009800 A1 | 1/2008 | Nickel | |
| 2008/0009801 A1 | 1/2008 | Nickel | |
| 2008/0009811 A1* | 1/2008 | Cantor | A61B 17/205 604/272 |
| 2008/0009825 A1 | 1/2008 | Ringsred et al. | |
| 2008/0108958 A1 | 5/2008 | Carter et al. | |
| 2010/0030152 A1 | 2/2010 | Lee et al. | |
| 2010/0228203 A1 | 9/2010 | Quan et al. | |
| 2010/0256568 A1* | 10/2010 | Frederickson | A61M 37/0015 604/173 |
| 2010/0258568 A1 | 10/2010 | Frederickson et al. | |
| 2012/0109067 A1* | 5/2012 | Ozawa | A61M 37/0015 604/173 |
| 2012/0184906 A1* | 7/2012 | McAllister | A61M 37/0015 604/136 |
| 2013/0006187 A1 | 1/2013 | Kobayashi et al. | |
| 2014/0243747 A1* | 8/2014 | Tokumoto | A61B 5/15117 604/173 |
| 2017/0266428 A1 | 9/2017 | Frederickson et al. | |

FOREIGN PATENT DOCUMENTS

| | | | |
|---|---|---|---|
| CN | 101068591 A | 11/2007 | |
| CN | 101076367 A | 11/2007 | |
| CN | 101208129 A | 6/2008 | |
| CN | 101557848 A | 10/2009 | |
| CN | 101687090 A | 3/2010 | |
| JP | 2002-517300 A | 6/2002 | |
| JP | 2003-238347 A | 8/2003 | |
| JP | 2004-510530 A | 4/2004 | |
| JP | 2004-510534 A | 4/2004 | |
| JP | 2004-510535 A | 4/2004 | |
| JP | 2005-533625 A | 11/2005 | |
| JP | 2006-500973 A | 1/2006 | |
| JP | 2007-509706 A | 4/2007 | |
| JP | 2008-520367 A | 6/2008 | |
| JP | 2011-78711 A | 4/2011 | |
| WO | WO-99/64580 A1 | 12/1999 | |
| WO | WO-02/30281 A1 | 4/2002 | |
| WO | WO-02/30300 A2 | 4/2002 | |
| WO | WO-02/30301 A1 | 4/2002 | |
| WO | WO-2004-000389 A2 | 12/2003 | |
| WO | WO-2004/009172 A1 | 1/2004 | |
| WO | WO-2005/044333 A2 | 5/2005 | |
| WO | WO-2006/055771 A1 | 5/2006 | |
| WO | WO-2011/089907 A1 | 7/2011 | |
| WO | WO-2012/000871 A1 | 1/2012 | |
| WO | WO-2012/054518 A1 | 4/2012 | |
| WO | WO-2012/088154 A1 | 6/2012 | |

OTHER PUBLICATIONS

International Search Report for the Application No. PCT/JP2013/075149 dated Dec. 24, 2013.
Written Opinion of the International Searching Authority (PCT/ISA/237) for Application No. PCT/JP2013/075149 dated Dec. 24, 2013.
Written Opinion of the International Searching Authority (PCT/ISA/237) for Application No. PCT/JP2013/075149 dated Dec. 24, 2013 (English Translation mailed Mar. 31, 2016).
The First Office Action for the Application No. 201380079632.5 from The State Intellectual Property Office of the People's Republic of China dated May 30, 2018.

* cited by examiner

MICRONEEDLE PATCH APPLICATION DEVICE AND PATCH HOLDER

TECHNICAL FIELD

The present invention relates to a microneedle patch application device for applying to a skin a microneedle patch for imparting contraction effects and/or functional effects to at least one of a surface layer and stratum corneum of the skin. Furthermore, the present invention relates to a patch holder used in combination with the microneedle patch application device.

BACKGROUND ART

As a method of administering a drug to a human body, oral administration and transdermal administration are often used. Although injection is a typical transdermal administration method, it is a procedure which takes time, is painful, and further is likely to cause an infection, so many people do not welcome the procedure. In contrast, a transdermal administration method without pain using a microneedle array has been recently attracting attention (Patent Document 1, Non-Patent Document 1).

In transdermal administration of a drug, skin stratum corneum works as a barrier to drug permeation, so only applying the drug on a skin surface does not necessarily cause enough permeability. In contrast, perforation of the corneum by using a minute needle, i.e. a microneedle can remarkably improve drug permeation efficiency compared to the application method. An article in which a large number of the microneedles are integrated on a substrate is a microneedle array. Furthermore, a product in which sheets such as an adhesive sheet for adhering the microneedle array to a skin or a protective release sheet for protecting and supporting the adhesive sheet when applying the microneedle array to a skin are added to the microneedle array in order to facilitate its use is called a microneedle patch. Herein, an adhesive sheet means a film, a fabric, or a paper to which an adhesive agent is applied.

When the microneedle is produced by using a substrate such as saccharide which disappears by metabolism in a body, an accident does not occur even if the needle is broken and remains in a skin. Furthermore, if a drug is contained in the saccharide, the drug can be easily administered into and under the skin by dissolving the inserted microneedle in the body (Patent Document 2).

However, since a skin is generally flexible, the microneedles cannot be easily inserted into the skin only by pressing the microneedle array with a finger when the microneedle array is administered to the skin. This is because a skin is elastic tissue originally with a role of defending various stimuli, impact, and the like from the outside world, so even if sharp tips of the microneedles are pressed against the skin, the skin absorbs the impact and deforms to prevent the entry of the microneedles into the skin.

For administering the microneedle array to a skin with the impact absorption capability, the microneedle array must be administered to the skin at high speed and with impact. As the method of the administration, utilization of a spring (Patent Documents 3-8), air pressure (Patent Document 7), magnetic force (Patent Document 9), or the like has been hitherto proposed. In order to make the spring easily usable for a woman or an infant, ingenuity is needed for a spring compression method and a trigger method. Also, the utilization of an pressure or magnetic force is not always simple.

The conventional microneedle array administration devices still have practical problems, so a simpler device with which insertion can be surely performed has been demanded by users.

PRIOR ART DOCUMENTS

Patent Documents

[Patent Document 1] JP 2002-517300 W
[Patent Document 2] JP 2003-238347 A
[Patent Document 3] JP 2004-510530 W (JP 4198985 B2)
[Patent Document 4] JP 2004-510534 W (JP 4104975 B2)
[Patent Document 5] JP 2004-510535 W (JP 4659332 B2)
[Patent Document 6] JP 2005-533625 W
[Patent Document 7] JP 2006-500973 W
[Patent Document 8] JP 2007-509706 W (JP 4682144 B2)
[Patent Document 9] JP 2011-078711 A

Non-Patent Document

[Non-Patent Document 1] Ying-Shu QUAN, Fumio KAMIYAMA "The Course of Development and Manufacturing for Microneedle", The Academy of Pharmaceutical Science and Technology, Japan; July 2009, Vol. 69, 4th issue, p. 272-276

SUMMARY OF INVENTION

Technical Problem

An object of the present invention is to provide a microneedle patch application device and a patch holder having simple structure, with which a microneedle array of a microneedle patch can be surely inserted into a skin.

Solution to Problem

The microneedle patch application device according to the present invention is for inserting a microneedle array into a skin, by pressing a microneedle patch provided with the microneedle array on a first surface of a patch body, from a second surface opposite to the first surface. The microneedle patch application device according to the present invention comprises: a casing body having, at one end, an opening through which the microneedle patch passes; a pressing member having a tip surface for pressing the second surface of the microneedle patch, the pressing member being disposed movably in a first direction, in which the microneedle array is moved outward through the opening, and a second direction opposite to the first direction in the casing body; a first biasing means provided in the casing body and disposed to bias the pressing member in the first direction; and a locking member connected to the casing body. The pressing member is provided with a locking part which is engaged with the locking member so as to regulate movement of the pressing member in the first direction. The microneedle patch application device further comprises a lock-releasing member having a protruding part disposed outside the opening of die casing body and protruding from a peripheral part of the opening of the casing body in the first direction, the lock-releasing member being movable in the second direction and being provided associated with the locking member so as to release a locked state in which the locking member is locked on the locking part when the protruding part moves in the second direction. A window part for inserting the microneedle patch is formed on a surface different from the surface provided with the opening of the casing body. According to the present invention, in order that a set state in which the tip surface of the pressing member is drawn from the opening along the second direction and faces the window part for inserting the microneedle patch and an application state in which the tip surface of the pressing member protrudes outside the opening of the casing body in the first direction can be taken, the locking member is in the locked state in the set state, and when the locked state is released with the lock-releasing member, the tip surface of the pressing member is moved by biasing force of the first biasing means to bring into the application state.

In a certain aspect of the microneedle patch application device according to the present invention, the device further comprises an operating member connected to the pressing member and provided movably to the casing body so as to move, the pressing member in the second direction.

In another certain aspect of the microneedle patch application device according to the present invention, the device further comprises a second biasing means for biasing the operating member in the first direction.

In another certain aspect of the microneedle patch application device according to the present invention, the casing body is a tubular part, one end of the tubular part is provided with the opening, and a side surface of the tubular part is provided with the window part for inserting the microneedle patch.

In another certain aspect of the microneedle patch application device according to the present invention, the biasing means is a pressing spring.

In another certain aspect of the microneedle patch application device according to the present invention, the lock-releasing member has a cylindrical part externally inserted to the tubular part.

In another certain aspect of the microneedle patch application device according to the present invention, the casing body has slots extending, in the first direction, and the operating member is connected to the casing body so as to be movable along the slots.

In another certain aspect of the microneedle patch application device according to the present invention, the operating member is connected to the pressing member so that the pressing member moves with the operating member in the second direction when the operating member is moved in the second direction.

In another certain aspect of the microneedle patch application device according to the present invention, the lock-releasing member is externally inserted to the casing body and provided movably to the casing body in the second direction opposite to the first direction, and the locked state of the locking member is released by moving the lock-releasing member in the second direction.

In another certain aspect of the microneedle patch application device according to the present invention, the locking member has a rotation axis and is provided rotatably around the rotation axis, and a third biasing means is further provided for biasing the locking member to the casing, body in one direction around the rotation axis so as to bring into the locked state.

In another certain aspect of the microneedle patch application device according to the present invention, the pressing member is moved so that impact energy provided to the microneedle patch to insert microneedles into a skin is within a range of 0.4-5.0 J.

A patch holder according to the present invention is inserted into the window part for inserting a microneedle patch of a microneedle patch application device constituted according to the present invention, the patch holder having a microneedle patch holding part for holding the microneedle patch, the microneedle patch holding part being provided with an opening for exposing a microneedle array, and the microneedle patch being adhesively held on at least one peripheral portion of the opening.

Advantageous Effects of Invention

With the microneedle patch application device according to the present invention, a microneedle patch can be surely applied to a skin surface, by drawing the pressing member into the casing body against biasing force of the first biasing means to bring into the locked state, by inserting the microneedle patch from the window part for inserting the microneedle patch, and then by abutting the lock-releasing member with the skin surface to release the locked state. Therefore, a microneedle patch application device with relatively simple structure for surely inserting a microneedle array into a skin can be provided.

DESCRIPTION OF EMBODIMENTS

Hereinafter, the present invention will become apparent from the following description of specific embodiments of the present invention with reference to the drawings.

Figure 1:
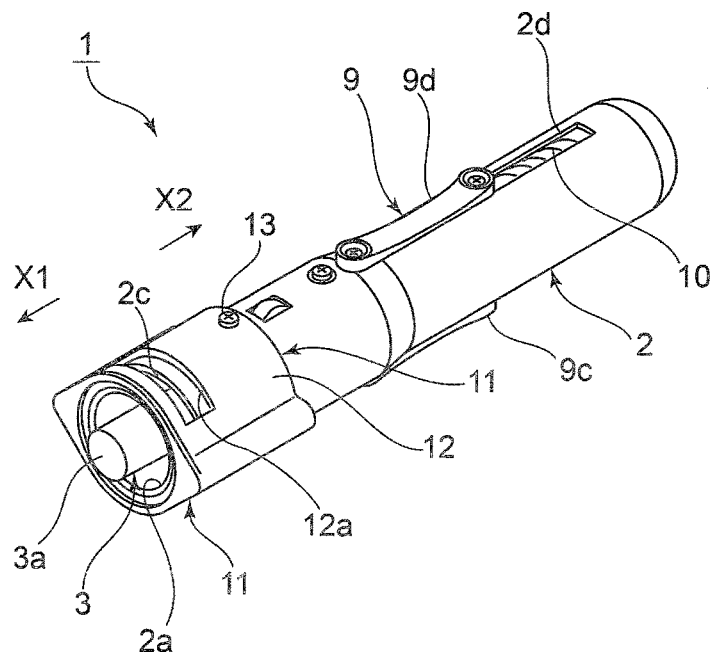
FIG. 1 is a perspective view of a microneedle patch application device according to an embodiment of the present invention.
Figure 2:
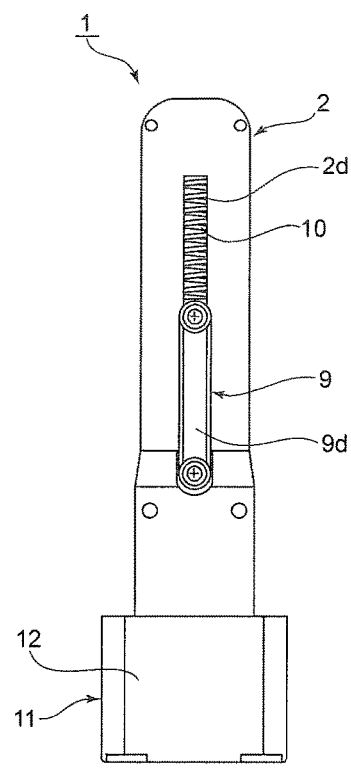
FIG. 2 is a front view of the microneedle patch application device shown in FIG. 1.
Figure 3:
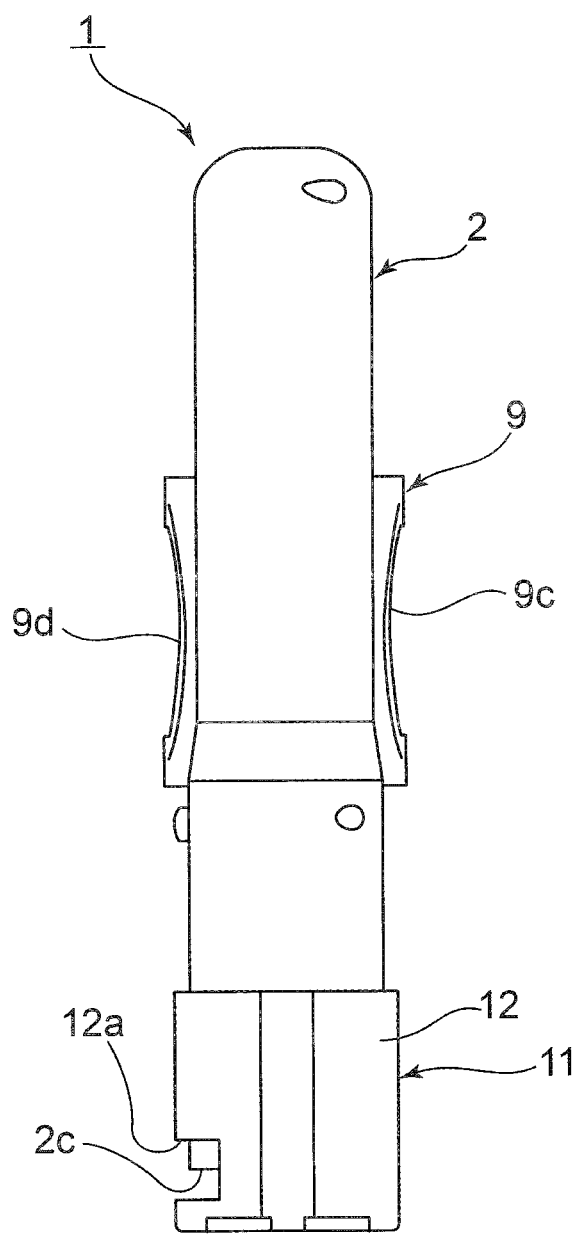
FIG. 3 is a side view of the microneedle patch application device shown in FIG. 1.

FIG. 1 is a perspective view showing an appearance of a microneedle patch application device according to an embodiment of the present invention, FIG. 2 is a front view of the microneedle patch application device, and FIG. 3 is a side view of the microneedle patch application device.

Figure 4:
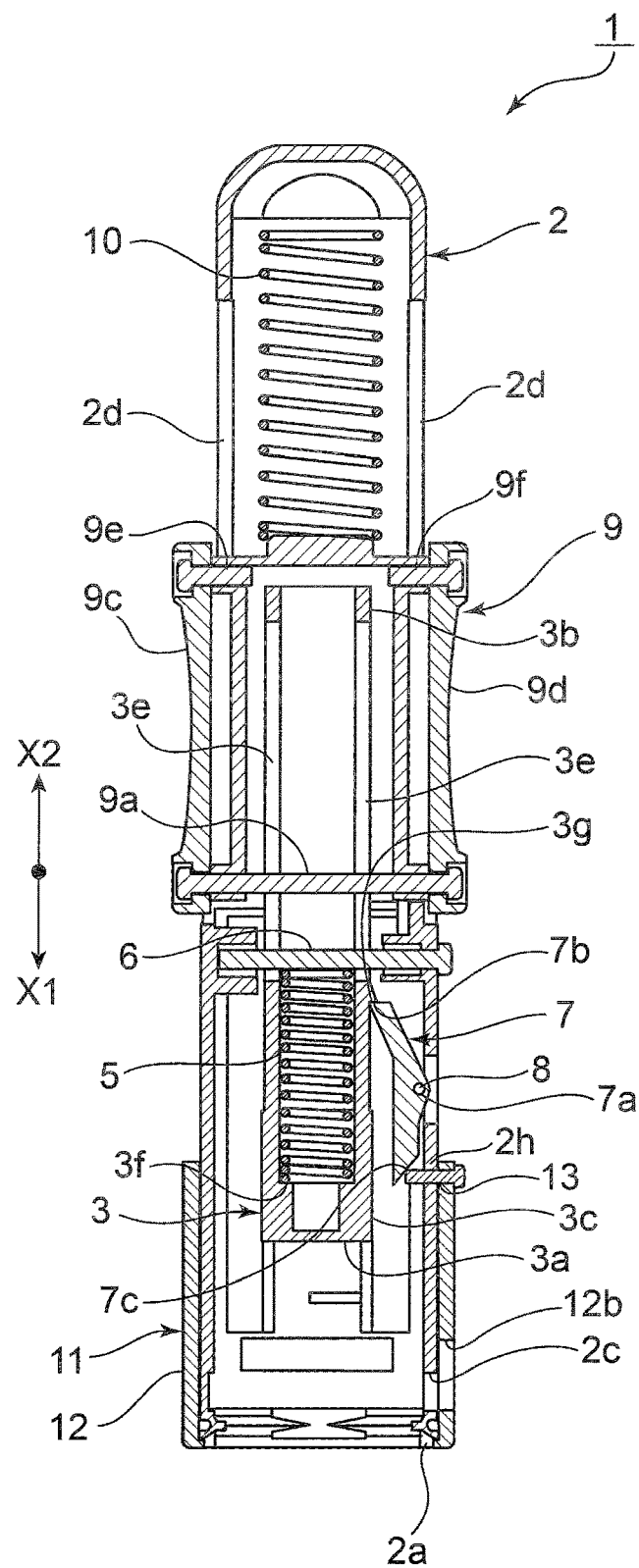
FIG. 4 is a sectional side view of the microneedle patch application device shown in FIG. 1.

Furthermore, FIG. 4 is a sectional side view of the microneedle patch application device. FIG. 1 shows a skin application state in which a pressing member protrudes from a easing body as described below. FIG. 2-FIG. 4 do not show the skin application state but a set state in which the pressing member is drawn into the casing body.

As shown in FIG. 1, the microneedle patch application device 1 has the cylindrical casing body 2. The casing body 2 can be formed of an appropriate rigid material such as synthetic resin or metal. Preferably, synthetic resin is used for lightweighting.

The casing body 2 has an opening 2a on one end side. A direction connecting the end provided, with the opening 2a and an opposite end is a longitudinal direction of the tubular body. A direction X1 of the longitudinal direction shown in FIG. 1-FIG. 4, i.e. a direction outward from the opening 2a is referred to as a first direction. Furthermore, a direction opposite to the first direction X1 is referred to as a second direction X2.

As shown in FIG. 1, the pressing member 3 is disposed so as to protrude from the opening 2a to the outside in the first direction X1. In FIG. 1, a tip surface 3a of the pressing member 3 is positioned outward from the opening 2a in the first direction X1. The tip surface 3a serves to press a second surface of a microneedle patch as described below In FIG. 4, the tip surface 3a of the pressing member 3 is positioned inward from the opening 2a in the direction X2. Namely, the pressing member 3 is drawn into the casing body 2.

Figure 5:
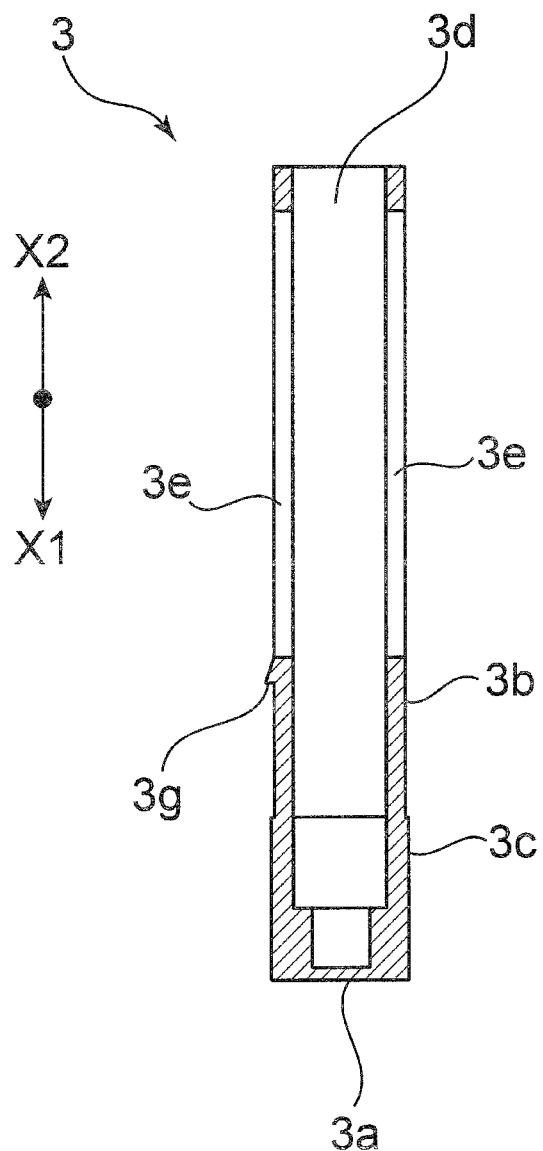
FIG. 5 is a sectional front view showing structure of a pressing member used in an embodiment of the present invention.
Figure 6:
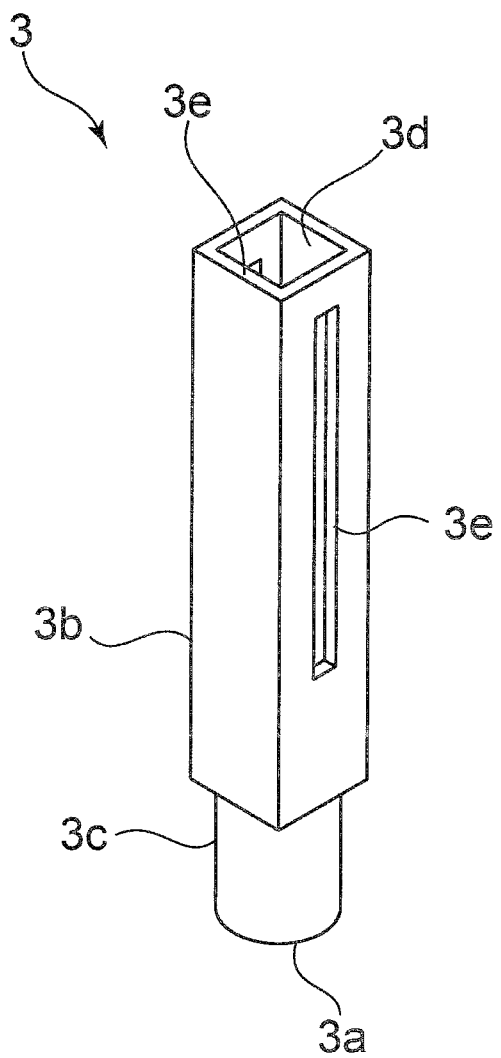
FIG. 6 is a perspective view of the pressing member used in an embodiment of the present invention.

As shown in FIGS. 5 and 6, in the present embodiment, the pressing member 3 has a rectangular cylindrical part 3b and a cylindrical part 3c continued to a tip of the rectangular cylindrical part 3b. A tip of the cylindrical part 3c is closed and constitutes the tip surface 3a as described above.

As shown in FIG. 6, the above pressing member 3 has a hollow part 3d extending in the longitudinal direction. The rectangular cylindrical part 3b is provided with slots 3e, 3e extending in first and second directions X1, X2 so as to communicate with an outside of the hollow part 3d. One slot 3e and the other slot 3e are formed on a pair of opposed side surfaces of the rectangular cylindrical part 3b.

The above pressing member 3 can be formed of a rigid material such as metal or synthetic resin. Although a planar shape of the tip surface 3a of the pressing member 3 is circular in the present embodiment, the tip surface 3a may have other shape such square or rectangle. Therefore, the pressing member 3 may be formed of only the rectangular cylindrical part 3b without the cylindrical part 3c.

In fact, since a planar shape of the microneedle patch as described below is circular in the present embodiment, it is desirable that the tip surface 3a has the circular shape.

As shown in FIG. 4, a pressing spring 5 as a first biasing means is inserted into the above pressing member 3. The pressing spring 5 is in a compressed state in FIG. 4. One end of the pressing spring 5 is locked by a step part 3f provided on an inner wall of the pressing member 3. Furthermore, the other end of the pressing spring 5 is abutted with a pressing spring stopper 6. The pressing spring stopper 6 can be constituted of a rod or a bolt inserted through the slots 3e, 3e as described above in the present embodiment. The pressing spring stopper 6 is fixed to the casing body 2.

Figure 7:
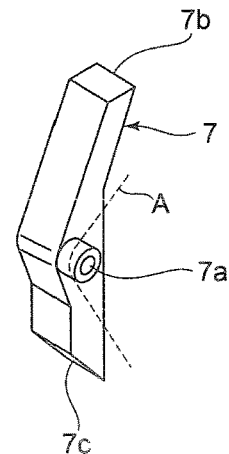
FIG. 7 is a perspective view of a locking member used in an embodiment of the present invention.
Figure 8:
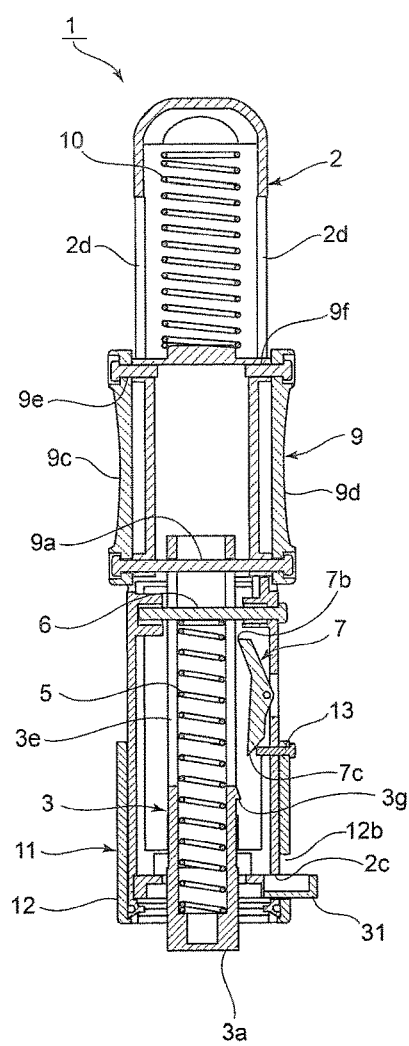
FIG. 8 is a sectional side view of the microneedle patch application device in an application state according to an embodiment of the present invention.

On the other hand, a locking member 7 is attached above the opening 2a of the casing body 2. FIG. 7 is a perspective view of the locking member. The locking member 7 has a through-hole 7a at the center of the longitudinal direction. A pin 8 is inserted into the through-hole 7a (see FIG. 4). The pin 8 is fixed to the casing body 2. The locking member 7 is connected to the casing body 2 so as to be displaceable around the center of the pin 8 as a rotation axis.

Furthermore, a spring A as shown with a virtual line in FIG. 7 is disposed around the above pin 8. The spring A as a third biasing means is bridged between the pin 8 and the locking member 7 to bias an engagement end 7b of the locking member 7 counterclockwise.

Therefore, the engagement end 7b of the locking member 7 is normally biased toward the pressing member 3 by biasing force of the above spring.

On the other hand, the side surface of the pressing member 3 is provided with a locking part 3g. The locking part 3g is provided so as to protrude from the side surface of the pressing member 3 to the outside. The locking part 3g is constituted of a step part extending in a direction intersecting with the first direction X1 and the second direction X2. The above engagement end 7b of the locking member 7 is engaged with the locking part 3g. FIG. 4 shows a locked state in which the locking member 7 is locked on the locking part 3g. In other words, the locking member 7 is in the locked state by being engaged on the locking part 3g so as to maintain the set state as described below.

The above locking, member 7 can be formed of synthetic resin, metal, or the like.

Figure 10:
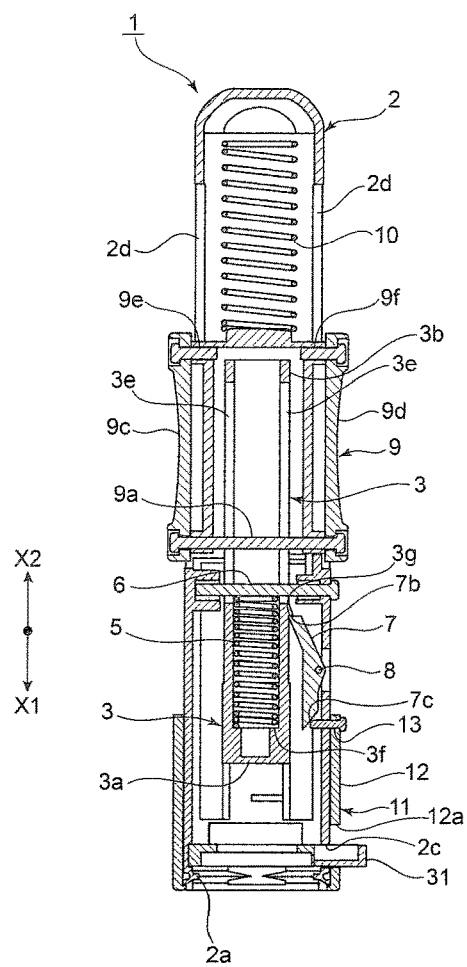
FIG. 10 is a sectional side view showing a state in which a microneedle patch holder is attached to the microneedle patch application device shown in FIG. 1.

As shown in FIGS. 1 and 4, a window part 2c for inserting a microneedle patch is provided near the opening 2a of the casing body 2. A patch holder 31 as described below is inserted into the window part 2c for inserting a microneedle patch. FIG. 10 shows a state in which the patch holder 31 is inserted through the window part 2c for inserting a microneedle patch.

As shown in FIG. 4, the above window part 2e for inserting a microneedle patch is positioned below the tip surface 3a of the pressing member 3 in the set state.

As shown in FIG. 4, a operating member 9 is connected above the above pressing member 3. The casing body 2 is provided with a pair of Slots 2d, 2d facing each other so as to extend in a central direction from nearby an end opposite to the opening 2a. The slots 2d, 2d are extended in the first and second directions X1, X2.

The operating member 9 has a connecting bar 9a, operating knobs 9c, 9d fixed to both ends of the connecting bar 9a, and pins 9e, 9f. The connecting bar 9a is across the tubular body and inserted through the above slots 2d, 2d. One end of the connecting bar 9a is fixed to a lower end of one operating knob 9c. The other end of the connecting bar 9a is fixed to a lower end of the other operating knob 9c. One ends of the pins 9e, 9f are fixed near upper ends of the operating knobs 9c, 9d. The other ends of the pins 9e, 9f reach into the slots 2d, 2d.

The, pins 9e, 9f and the connecting bar 9a function as a guide when the operating knob 9d moves in a direction in which the slots 2d, 2d extend. Furthermore, the above connecting bar 9a is also inserted through the slits 3e, 3e of the pressing member 3 as described above.

On the other hand, a pressing spring 10 as a second biasing means is disposed above the operating member 9. The pressing spring 10 is contained in the casing body 2, and the operating member 9 is biased in the first direction X1 by the pressing spring 10.

The above operating member 9 can be also formed of a appropriate rigid material such as metal or synthetic resin.

Figure 9:
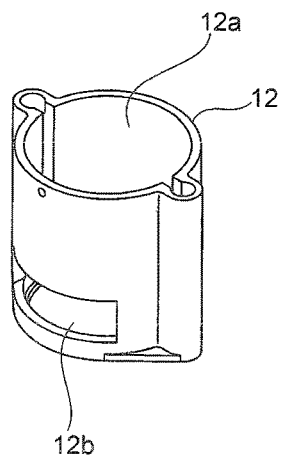
FIG. 9 is a perspective view of a tubular body of a lock-releasing member used in an embodiment of the present invention.

Furthermore, the above microneedle patch application device 1 has a lock-releasing member 11. The lock-releasing member 11 has a tubular member 12 shown in FIG. 9. The tubular member 12 has an opening 12a. The lock-releasing member 11 is externally inserted to the cylindrical casing body 2 through the opening 12a. Furthermore, a side surface near a lower end of the tubular member 12 is provided with an opening 12b for inserting a microneedle patch. In FIG. 4, the opening 12b for inserting a microneedle patch is provided at a position overlapping with the window part 2c for inserting a microneedle patch of the tubular casing body 2.

As shown in FIG. 4, a pin 13 is fixed to the tubular member 12 of the lock-releasing member 11. The pin 13 is extended into the casing body 2. The casing body 2 is provided with a short slit 2h extended in an up-and-down direction. The pin 13 is extended into the slit 2h. Therefore, the above lock-releasing member 11 is movable up and down by length of the above slit 2h. On the other hand, a tip of the pin 13 is abutted with an inclined wall 7c of the locking member 7. When the pin 13 moves up, the inclined wall 7c is pushed by the tip of the pin 13, so the locking member 7 is moved around the rotation axis as described above clockwise. Thereby, the engagement end 7b of the locking member 7 is released from the locking part 3g to bring into a lock-releasing state.

Namely, the locking member 7 is biased so as to rotate around the rotation axis counterclockwise so that the locked state is normally maintained by the biasing force of the spring as not shown but described above. When the lock-releasing member 11 is moved up against the biasing force, the above pin 13 is abutted with the inclined wall 7c to displace the locking member 7 around the above rotation axis clockwise. Therefore, the engagement end 7b is released from the locking part 3g to release the locked state.

Next, an application method of a microneedle patch using the microneedle patch application device 1 according to the present embodiment is described.

First, in a default position, the tip surface 3a of the pressing member 3 is in the set state as shown in FIG. 4. In this position, the engagement end 7b of the locking member 7 is locked on the locking part 3g in the locked state. Thereby, the state shown in FIG. 4 is maintained. Since the tip surface 3a is drawn upward, the patch holder 31 shown in FIGS. 11 and 12 can be inserted through the window part 2c for inserting a microneedle patch of the casing body 2 and the opening 12b for inserting a microneedle patch of the tubular member 12 of the lower lock-releasing member 11. The patch holder 31 has a holding part 36 where a microneedle patch is held. The holding part 36 is provided with an opening 35 smaller than the microneedle patch.

A microneedle patch has an adhesive surface, with which the microneedle patch is applied on a lower surface of the holding part 36. Thereby, the microneedle patch is easily set to the patch holder 31. Furthermore, although the microneedle patch is a thin member with flexibility, it is made easy to handle by being set to the patch holder 31.

Then, after the patch holder 31 has been inserted as shown in FIG. 10, the tip of the microneedle patch application device 1 is abutted and press-contacted to a skin surface to be applied. By the contact pressure, reaction force is added to the tip of the tubular member 12 of the lock-releasing member 11. By the reaction force, the lock-releasing member 11 is pushed in the second direction X2 and moved. As a result, the locking member 7 rotates clockwise as described above to release the locked state. When the locked state is released, by elastic force of the pressing spring 5 as the first biasing means, the tip surface 3a of the pressing member 3 moves in the first direction X1 to bring into the application state. Therefore, the tip surface 3a can press a back surface, or the second surface of the microneedle patch. The microneedle patch will be applied to the skin surface by the pressing force given by the tip surface 3a.

Then, for returning the device to the first set state shown in FIG. 4, the operating member 9 is withdrawn upward from the application state shown in FIG. 4, in which the patch holder 31 is not shown. Namely, the operating member 9 is moved up along the slots 2d, 2d. As a result, the pressing member 3 connected to the operating member 9 is drawn back in the second direction X2 with the operating member 9. The device is brought into the locked state at a stage where the locking part 3g of the pressing member 3 is beyond the engagement end 7b of the locking member 7. Then, the patch holder may be removed. Therefore, the device will be returned to the delimit set state shown in FIG. 4.

Therefore, when the microneedle patch application device 1 according to the present embodiment is used, a microneedle patch can be easily and surely applied to a skin surface only by inserting the patch holder 31 in which the microneedle patch has been contained into the device in the set state and by pressing the tip of the lock-releasing member 11 against the skin surface. After the application, the device can be easily and immediately returned to the default set state only by operating the operating member 9.

According to the present embodiment, a microneedle patch can be easily and surely applied to a skin surface by using the microneedle patch application device with simple structure.

Although the casing body 2 is the tubular body in the above embodiment, it may be a shape other than the tubular body.

Furthermore, although the pressing spring 10 as the second biasing means is used in the above embodiment, the second biasing means may be omitted. Moreover, the operating member 9 may be omitted, and in this case the tip surface 3a may be moved in the second direction X2 with a finger or the like, for example, against the elastic force of the pressing spring 5 as the first biasing means, to bring into the set state.

Furthermore, in the above microneedle patch application device 1, by adjusting the elastic force of the above pressing spring 5 as the first biasing means, impact force when a microneedle patch is applied to a skin with the tip surface 3a can be easily adjusted. According to an experiment of the inventors, it is confirmed that, in order to surely insert a microneedle array into a skin, the pressing member 3 is preferably moved so that the above impact energy is within a range of 0.4-5.0 J. Therefore, the elastic force of the pressing spring 5 should be adjusted to provide the impact energy within the range.

Next, specific examples and comparative example are described. The present invention is not limited to the following examples.

EXAMPLE 1

Elasticity change of a skin when the skin was compressed by the tubular member 12 of the lock-releasing member 11 was measured with a skin viscoelasticity measuring device (Integre Corporation, CUTOMETER MPA580). According to the measurement in a standard measurement method (mode 1), a value R2 indicating overall pressure was 0.633 when the skin was not compressed, and 0.835 when the skin was compressed. Since higher elasticity is closer to 1.0, it was quantitatively shown that the elasticity was improved by the compression.

A prototype microneedle patch application device had a pressing member 3 with a weight of 7.2 g, a displacement amount of 29.6 mm, a spring constant of 0.258 N/mm, a (theoretical) moving speed upon shot of 5.6 m/s, and an impact energy of 4.0 J.

Figure 11:
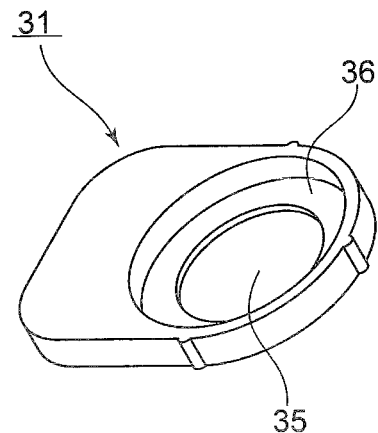
FIG. 11 is a perspective view of a patch holder used in an embodiment of the present invention.
Figure 12:
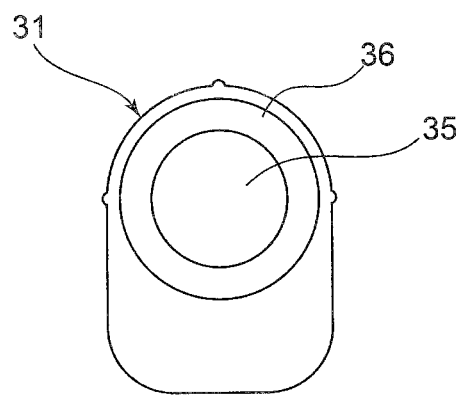
FIG. 12 is a plan view of the patch holder used in an embodiment of the present invention.

A patch holder 31 used in the present example is shown in FIGS. 11 and 12 described above. The patch holder 31 is made of polyethylene, is intended to hold a microneedle patch in which a circular adhesive sheet with a diameter of around 22 mm is attached to a circular microneedle array with a diameter of around 12 mm, and has an opening 35 with a diameter of 16 mm and a peripheral edge with an amplitude of 4 mm.

In order to impart weak adhesiveness to the peripheral edge, HiPAS adhesive agent (produced by CosMED Pharmaceutical Co. Ltd) was applied in a thickness of 10 µm. The microneedle patch was held on the holding part 36 with the adhesiveness.

The patch holder 31 has a handle. The handle is used for holding the patch bolder when the patch bolder 31 is inserted from a side opening of the tubular member 12 of the lock-releasing member 11.

Figure 13:
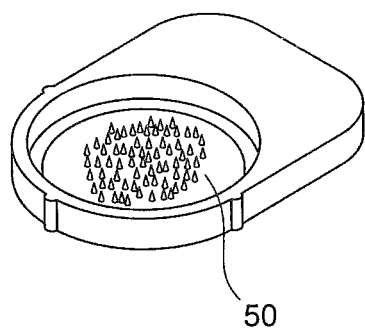
FIG. 13 is a perspective view showing a state in which a microneedle patch is set on the patch holder according to an embodiment of the present invention.

FIG. 13 is a perspective view of the microneedle patch 50 mounted on the lower surface of the holding part 36 of the patch holder 31. An adhesive tape surface of the microneedle patch is applied on the lower surface of the holding pan 36. The patch holder 31 holding the microneedle patch was taken from a packaging bag and then attached to the microneedle patch application device 1 in the set state in which the pressing member 3 was withdrawn.

EXAMPLE 2

A microneedle patch application device in Example 2 is similar to the application device in Example 1 except that the locking member 7, the pin, and the locking part 3g are in positions shifted by 90 degrees around a central axis of the casing body 2 in comparison with the application device in Example 1. Even if the structure is so modified, performance as a microneedle patch application device does not change.

Figure 14:
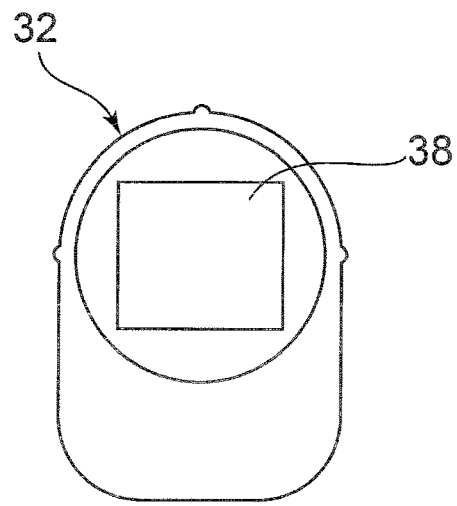
FIG. 14 is a plan view of a patch holder used in Example 2.

In Example 2, a patch holder 32 with a quadrangular opening 38 was used as shown in FIG. 14. The patch holder 32 is intended to hold a microneedle patch in which the circular adhesive sheet with a diameter of around 22 mm is attached to a square microneedle array with a side of 14 mm. The opening 38 is a square with a side of 15 mm, and an external diameter of a peripheral edge is 24 mm.

Even if the shape was so changed, performance and usability of the microneedle patch application device did not change.

EXAMPLE 3

In the present example, an application device is the same as that in Example 1 except that the patch holder is different.

Figure 15:
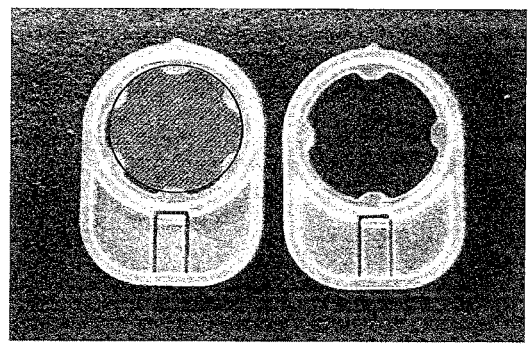
FIG. 15 is a plan view of a patch holder used in Example 3.

The patch holder used in Example 3 holds the microneedle array on an upper surface of a peripheral edge with the adhesive sheet of the microneedle patch. FIG. 15 is a photograph showing the state. The patch holder is intended to hold the microneedle patch in which the circular adhesive sheet with a diameter of around 22 mm is attached to the circular microneedle array with a diameter of around 12 mm.

Since the adhesive sheet of the microneedle patch has strong adhesive strength, the microneedle patch is preferably held on a part of the peripheral edge. Specifically, the periphery is provided with six projections on the left side of the photograph in FIG. 15. The periphery is provided with four projections on the right side of the photograph in FIG. 15. Thereby, when impact of the pressing member 3 is applied, the adhesive sheet might be damaged, so the microneedle patch may be hardly held on a skin surface.

On the left side of the photograph in FIG. 15, a position of the held microneedle patch is shown by a black circle.

EXAMPLE 4

Figure 16:
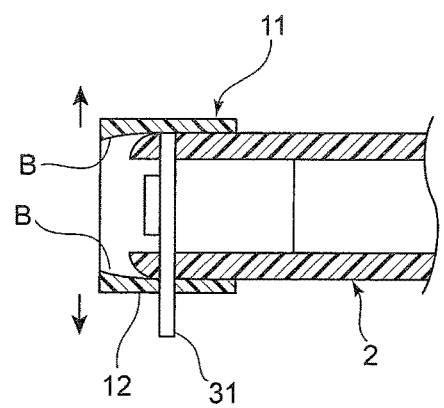
FIG. 16 is a partially cutaway sectional view for describing, a principal part of a microneedle patch application device used in Example 4.

In the microneedle patch application device in Example 1, the tubular member 12 of the lock-releasing member 11 in the tip was made of silicone rubber. When the tubular member 12 is pressed against a skin, the skin surface temporarily has high elasticity, so insertion of the microneedles becomes easier and more certain. In order to more ensure the effect, it is preferable that the tubular member 12 is made of silicone rubber and that an opening inner peripheral side of a tip portion is slightly upheaved inward as indicated by an arrow B in FIG. 16. Therefore, when the microneedle patch application device is pressed against a skin, the tubular member 12 is pushed by the casing body 2 and thereby expanded outward, so the skin can be more pulled to more enhance elasticity.

REFERENCE NUMERALS

1 Microneedle patch application device
2 Case body
2a Opening
2c Window part for inserting a microneedle patch
2d Slot
2h Slit
3 Pressing member
3a Tip surface
3b Rectangular cylindrical part
3c Cylindrical pan
3d Hollow part
3e Slot
3f Step part
3g Locking part
5 Pressing spring
6 Pressing spring stopper
7 Locking member
7a Through-hole
7b Engagement end
7c Inclined wall
8 Pin
9 Operating member
9a Connecting bar
9c, 9d Operating Knob
9e, 9f Pin
10 Pressing spring
11 Lock-releasing member
12 Tubular member
12a Opening
12b Opening for inserting a microneedle patch
13 Pin
31 Patch holder
32 Patch holder
35 Opening
36 Holding part
38 Opening 50 Microneedle patch
A Spring
X1 First direction
X2 Second direction

The invention claimed is:

1. A microneedle patch application device for inserting a microneedle array into a skin, by pressing a microneedle patch provided with the microneedle array on a first surface of a patch body, from a second surface opposite to the first surface,
wherein:
the microneedle patch application device comprises:
a casing body having, at one end, an opening through which the microneedle patch passes;
a pressing member having a tip surface for pressing the second surface of the microneedle patch, the pressing member being disposed movably in a first direction, in which the microneedle array is moved outward through the opening, and a second direction opposite to the first direction in the casing body;
a first biasing means provided in the casing body and disposed to bias the pressing member in the first direction: and
a locking member connected to the casing body,
the pressing member is provided with a locking part which is engaged with the locking member so as to regulate movement of the pressing member in the first direction,
the microneedle patch application device further comprises a lock-releasing member having a protruding part disposed outside the opening of the casing body and protruding from a peripheral part of the opening of the casing body in the first direction, the lock-releasing member being movable in the second direction and being associated with the locking member so as to release a locked state in which the locking member is locked on the locking part when the protruding part moves in the second direction,
a window part for inserting the microneedle patch is formed on a surface of the casing body and is spaced apart from the opening of the casing body,
wherein when the locking member is in the locked state in a set state of the microneedle patch application device in which the tip surface of the pressing member is drawn from the opening along the second direction and faces the window part for inserting the microneedle patch and when the locked state is released with the lock-releasing member, the tip surface of the pressing member is moved by biasing force of the first biasing means to bring the microneedle patch application device into an application state in which the tip surface of the pressing member protrudes outside the opening of the casing body in the first direction,
the casing body is a tubular part, one end of the tubular part is provided with the opening, a side surface of the tubular part is provided with the window part for inserting the microneedle patch, and
the microneedle patch application device further comprises a patch holder inserted into the window part to insert the microneedle patch into the microneedle patch application device,
wherein:
the patch holder has a microneedle patch holding part for holding the microneedle patch;
the microneedle patch holding part is provided with an opening for exposing the microneedle array; and
the microneedle patch is adhesively held on at least one peripheral portion of the opening of the microneedle patch holding part.

2. The microneedle patch application device according to claim 1, further comprising an operating member that is formed of a rigid material and is connected to the pressing member and provided movably to the casing body so as to move the pressing member in the second direction.

3. The microneedle patch application device according to claim 2, further comprising a second biasing means for biasing the operating member in the first direction.

4. The microneedle patch application device according to claim 2, wherein: the casing body has slots extending in the first direction: and the operating member is connected to the casing body so as to be movable along the slots.

5. The microneedle patch application device according to claim 4, wherein the operating member is connected to the pressing member so that the pressing member moves with the operating member in the second direction when the operating member is moved in the second direction.

6. The microneedle patch application device according to claim 5, wherein:
the lock-releasing member is externally inserted to the casing body and provided movably to the casing body in the second direction opposite to the first direction; and
the locked state of the locking member is released by moving the lock-releasing member in the second direction.

7. The microneedle patch application device according to claim 1, wherein the first biasing means is a pressing spring.

8. The microneedle patch application device according to claim 1, wherein the lock-releasing member has a cylindrical part externally inserted to the tubular part.

9. The microneedle patch application device according to claim 1, wherein: the locking member has a rotation axis and is provided rotatably around the rotation axis: and the microneedle patch application device further comprises a third biasing means for biasing the locking member to the casing body in one direction around the rotation axis so as to bring the locking member into the locked state.

10. The microneedle patch application device according to claim 1, wherein the pressing member is moved so that an impact energy provided to the microneedle patch to insert microneedles into a skin is within a range of 0.4-5.0 J.

* * * * *